United States Patent

Dimarogonas

[11] Patent Number: 5,836,876
[45] Date of Patent: Nov. 17, 1998

[54] METHOD AND APPARATUS FOR DETERMINING BONE DENSITY AND DIAGNOSING OSTEOPOROSIS

[75] Inventor: Andrew D. Dimarogonas, St. Louis, Mo.

[73] Assignee: Washington University, St. Louis, Mo.

[21] Appl. No.: 414,274

[22] Filed: Mar. 31, 1995

Related U.S. Application Data

[63] Continuation-in-part of Ser. No. 25,941, Mar. 3, 1993, Pat. No. 5,402,781.

[51] Int. Cl.$^6$ ........................................................ A61B 5/05
[52] U.S. Cl. .......................... 600/407; 600/437; 600/552; 600/553; 73/579; 73/584
[58] Field of Search ........................... 128/653.1, 660.01, 128/739, 740, 744, 660.03; 73/579, 584; 364/413.02; 600/407, 437, 439, 552, 553, 557

[56] References Cited

U.S. PATENT DOCUMENTS

| | | | |
|---|---|---|---|
| 3,744,299 | 7/1973 | Bliss . | |
| 3,847,141 | 11/1974 | Hoop | 128/660.01 |
| 4,361,154 | 11/1982 | Pratt, Jr. | 128/660.01 |
| 4,754,763 | 7/1988 | Doemland | 128/739 |
| 4,799,498 | 1/1989 | Collier | 128/774 |
| 4,926,870 | 5/1990 | Brandenburger | 128/660.01 |
| 4,941,474 | 7/1990 | Pratt, Jr. | 128/660.01 |
| 4,976,267 | 12/1990 | Jeffcott et al. | 128/660.01 |
| 5,006,984 | 4/1991 | Steele | 364/413.27 |
| 5,143,069 | 9/1992 | Kwon et al. | 128/660.01 |
| 5,195,532 | 3/1993 | Schumacher et al. | 128/740 |
| 5,210,704 | 5/1993 | Husseiny . | |
| 5,348,009 | 9/1994 | Ohtomo et al. | 128/653.1 |
| 5,402,781 | 4/1995 | Dimarogonas | 128/653.1 |

FOREIGN PATENT DOCUMENTS

| | | | |
|---|---|---|---|
| 91/06245 | 5/1991 | WIPO | 128/739 |

OTHER PUBLICATIONS

*The American Society of Mechanical Engineering* paper entitled Structural Damping, 1959, pp. 1–34.
*Calcified Tissue International* article entitled Material Damping for Monitoring of Density and Strength of Bones, by Andrew D. Dimarogonas et al., 1993, 52:244–247.

*Primary Examiner*—Brian L. Casler
*Attorney, Agent, or Firm*—Howell & Haferkamp, L.C.

[57] ABSTRACT

The density of a discrete piece of hard tissue such as a bone in a patient may be determined by either of two methods. In a first method, an impulse of energy is introduced into the tissue, and the resulting vibration in the hard tissue is sensed and analyzed to compute the modal damping factor of the tissue, the modal damping factor being directly related to the density of the tissue. In a second method, a continuous energy input is introduced into the hard tissue. The resulting vibration in the tissue is measured with a mechano-electrical vibration transducer and a modal damping factor is calculated. The electro-mechanical vibration transducer of the preferred embodiment measures the pressure with which the transducer is pressed against the patient's flesh and only produces the continuous energy input when a predetermined pressure is achieved which is sufficient to prevent any significant vibration of the flesh surrounding the bone. Further, the transducer signals the user if too great a pressure is applied to the patient's flesh. An algorithm is used with a microprocessor to estimate the modal damping factor of the hard tissue by varying several parameters until the difference between the measured response of the hard tissue and a theoretical response is minimized.

10 Claims, 3 Drawing Sheets

METHOD AND APPARATUS FOR DETERMINING BONE DENSITY AND DIAGNOSING OSTEOPOROSIS

This application is a continuation-in-part of U.S. patent application Ser. No. 08/025,941 filed Mar. 3, 1993, entitled, "Method and Apparatus for Determining Bone Density and Diagnosing Osteoporosis", U.S. Pat. No. 5,402,781.

BACKGROUND AND SUMMARY OF THE INVENTION

Studies of bone strength in vitro have demonstrated that decreases in bone strength in both the spine and femur are directly proportional to bone mineral content. For this reason, bone densitometry has been used extensively for the determination of bone loss in clinical diagnosis and monitoring. A variety of methods have been used, such as single and dual photon absorptiometry and quantitative computer tomography. However, these methods are time-consuming, dependent upon the availability of sophisticated and expensive equipment, and thus expensive and ill-suited for widespread implementation. As a result, there has been a long-felt need in the art for a simple, efficient, and low cost methodology for measuring bone density as density is an effective indicator of the onset of osteoporosis, a debilitating disease commonly found in post-pregnancy and post-menopausal women. Treatment of osteoporosis is most effective if the disease is detected early whereupon hormonal treatment may be commenced. However, because of the increased risk of side effects, it is undesirable to begin hormonal treatment until the disease has been detected. Additionally, measurement of bone density over time may be used to determine the effectiveness of treatment, leading to adjustments in the treatment protocols balanced against the attendant side effect risk.

Still another medical situation in which bone integrity is important is the healing process of bone fractures. There is a phenomenon known as non-union healing in which a bone fracture fails to knit properly to return the bone to its pre-fracture integrity. Obviously, x-rays may be used to monitor the healing process, but this methodology is expensive and undesirable in that it repeatedly exposes a body part to radiation. The inventor has previously participated in studies which noted the relationship of the vibrational response, and specifically the determination of the natural frequency shift and phase angle shift as being related, indirectly, to the progress of fracture healing. This previous experimental work used cadaver bones and its application to living patients is limited for the reasons discussed in his previously published article. See "Monitoring of Fracture Healing Bilateral and Axial Vibration Analysis," *Journal of Biomechanics,* Vol. 23, No. 4, 1990.

In order to solve these and other problems in the prior art, the inventor has succeeded in developing a method and apparatus for determining bone integrity by measuring the vibrational response of the bone to a stimulus and determining the modal damping factor of the bone from the response.

In general, the inventor has developed two techniques for measuring the modal damping factor of any bone or other hard tissue. Both techniques include the basic method of coupling a mechano-electrical vibration transducer to the bone. The transducer senses the vibrational response and produces an electrical output which is proportional to the vibrational response. A programmed electronic logic device such as a computer may be used to determine the modal damping factor from the electrical output of the transducer.

In a first implementation of this method, an impulse of energy is applied to the bone, such as by striking the flesh surrounding the bone, in order to generate a vibration in the bone at the lowest natural frequency of the bone. This vibration has a decreasing amplitude which may be measured and used to calculate the modal damping factor. In a second implementation of this same method, a continuous input of energy is applied to the bone, such as by driving a speaker or other electro-mechanical vibration transducer with a frequency generator and coupling the speaker to the bone, such that a continuous vibrational input is provided at about a natural frequency of the bone. Ideally, the frequency of the energy output from the frequency generator is adjustable so that it may be tuned to a natural frequency of the bone. The same transducer and computer may then be used to calculate the modal damping factor through a different mathematical analysis which depends upon the half power bandwidth and center frequency of the vibrational response of the bone.

One of the difficulties found in implementing the methods described above is that not only does the bone vibrate in response to the input, but also the flesh surrounding the bone vibrates. The sensors used to measure the bone vibration also pick up the vibration of the flesh. Because the bone and flesh vibrate at different natural frequencies and the vibration of each is affected by the other, the resulting output signal does not behave like a theoretical one degree of freedom system. Rather, the output signal has noise which can mask the desired signal. Thus, the computational analysis of the results becomes somewhat unwieldy.

The inventor has overcome this problem by developing a vibrator apparatus which compresses the flesh while vibrating the bone. Compressing the flesh raises its natural frequency and dampens its response sufficiently to reduce the amplitude of the vibrational response of the flesh without affecting the amplitude of the vibrational response of the bone. Therefore, a relatively noise-free bone response which approaches a theoretical one degree of freedom system is produced when the bone is excited with the vibrator apparatus of the present invention. Further, the vibrator only vibrates when sufficient pressure is applied to the flesh to sufficiently reduce its response and includes an indicator for signaling the user if too great a pressure which could cause injury or discomfort is applied to the flesh. Vibration and force sensors are also built into the apparatus of the preferred embodiment to improve the control of the apparatus and reduce the need for some external instrumentation.

Although the dynamic response of the flesh may be significantly reduced, it is not completely eliminated with the vibrator apparatus of the present invention. Therefore, the response received from the bone contains some noise even though the vibrator apparatus is used to excite the bone. Further, digital computer analysis techniques typically sample data at time intervals. This discrete sampling presents inaccuracies and computational difficulties in analyzing the bone response as is well known in the art and further compounds the analysis difficulties due to noise.

In order to solve these problems caused by noise and discrete sampling, the inventor has succeeded in developing a computer algorithm which estimates the modal damping factor from discrete vibration data received from the bone. The algorithm matches the measured response with a theoretical one degree of freedom system response and varies the theoretical system parameters until a suitable correlation between the theoretical and actual responses is achieved. When the suitable correlation is achieved, the actual bone modal damping factor is estimated to be that of the theoretical system. In proving the efficacy of the methodology disclosed and claimed herein, the inventor has conducted several experiments on bones. In doing so, the inventor has discovered that the change in the modal damping factor is one order of magnitude greater than the corresponding change in bone density. Thus, measurement of the modal damping factor is sensitive to and useful in determining bone density.

Furthermore, although it is desirable to locate the vibration transducer close to the bone in order to increase the gain of the measured vibrational response and decrease noise from other structures to thereby minimize measurement errors, it has been found that the flesh which surrounds the bone has little affect on the measurement because the bone dominates the vibrational response and therefore the modal damping factor at the lower natural frequencies. Thus, the vibration transducer may be mounted on the skin and the measurements may be taken through the flesh surrounding the bone. Thus, no penetration of the skin is required to make the measurement.

Still further, as the modal damping factor is a measure of the loss of strain energy during one vibratory cycle in the stress bearing part of the bone, it is relatively insensitive to boundary conditions such as the support given the bone and the characteristics of the surrounding flesh. On the other hand, other dynamic properties, such as the natural frequency used in the inventor's prior published article, vary significantly when the boundary conditions change, and are not nearly as sensitive to changes in density, which makes these dynamic properties impractical to use in measuring and monitoring bone density levels and changes in the density over time.

The inventor's approach of using the modal damping factor as an indicator of bone density is also intellectually satisfying in that there is a rationale for the experimentally measured variations in the modal damping factor. It is generally understood and believed that loss of mass, or decrease in density, of a bone is due to the loss of minerals and a resultant void nucleation that, in turn, results in stress concentration and premature fracture. This void nucleation is detected by a change in the modal damping factor as the bone becomes more porous which decreases the bone stiffness and increases the bone damping. Thus, the measurement of the modal damping factor is seen to be a direct measurement of this void nucleation and, hence, a direct indication of the integrity of the bone.

The inventor's techniques may be readily applied to the diagnosis and treatment of osteoporosis. In the first instance, the density of a particular bone of a patient may be estimated by measuring the modal damping factor, and the modal damping factor may be determined in the same manner at various intervals of time as the patient is treated. These modal damping factors taken at various time intervals may be compared to detect any changes which would indicate a change in bone density. A decrease in bone density in medically significant amounts indicates the onset of osteoporosis. Alternately, it would be hoped that treatment, perhaps through exercise, would be helpful in increasing or at least forestalling the decrease in bone density. Thus, these techniques may be useful in measuring the effectiveness of treatments so that treatment protocols may be altered over time as the patient is treated. This methodology and use of the modal damping factor depends upon a relative comparison of modal damping factor measurements for the same bone in the same patient over time.

An alternate methodology takes advantage of standardized modal damping factors or bone density values, yet to be determined, for patients and bones having various characteristics such as age, sex, fitness level, bone type. Using this alternate method, a particular patient's bone density or modal damping factor measurement may be compared to the standardized values in order to determine their potential for having osteoporosis. As the inventor has recently developed the present invention, there has not been an opportunity to determine these standardized values. However, it is believed to be a straightforward matter for one of ordinary skill in the art to use the present invention and measure a statistically significant group of individuals in order to determine these standardized values and the particular factors important in differentiating members of the group.

While the principal advantages and features of the present invention have been described above, a more complete and thorough understanding of the invention may be attained by referring to the drawings and description of the preferred embodiment which follow.

BRIEF DESCRIPTION OF THE DRAWINGS

Further objects and features of the present invention are revealed in the following Detailed Description of the Preferred Embodiment of the invention and in the drawing figures wherein.

DETAILED DESCRIPTION OF THE PREFERRED EMBODIMENT

Figure 1:
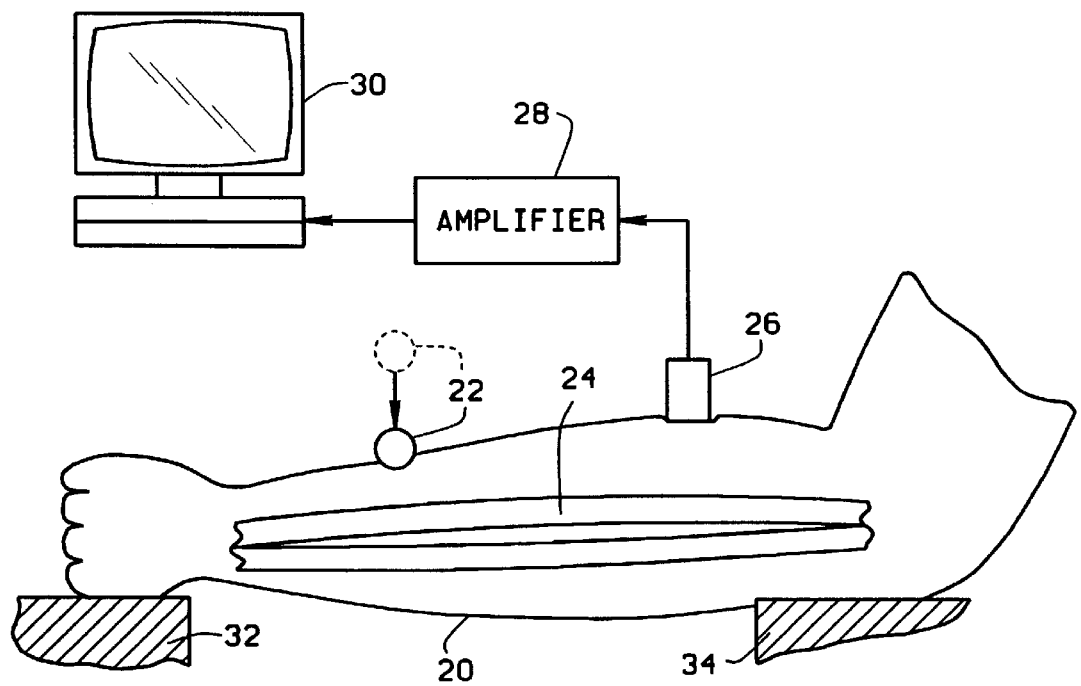
FIG. 1 is a diagrammatic view of a first technique for measuring bone density by inputting an impulse of energy to induce a vibration into the bone.
Figure 2:
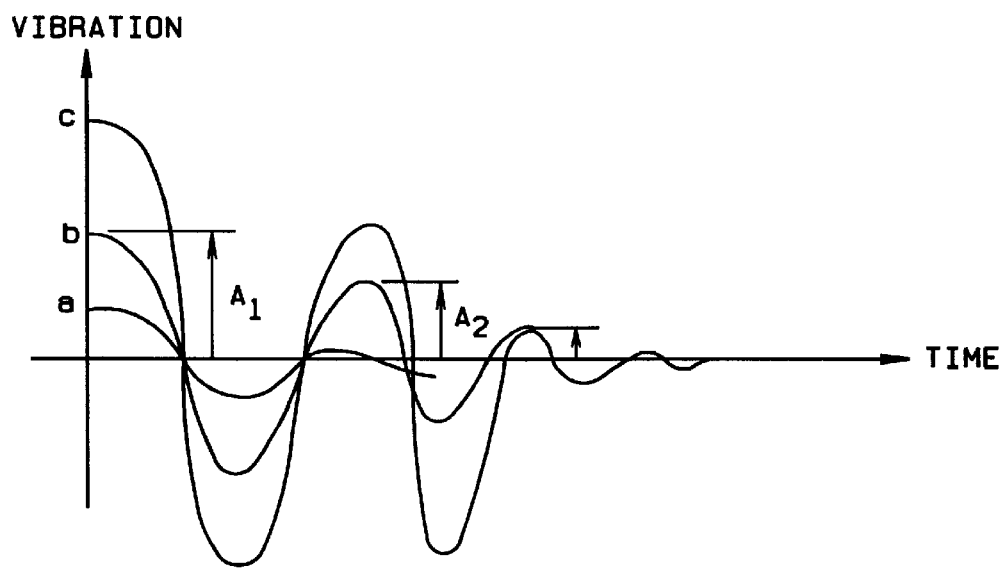
FIG. 2 is a graph of the harmonic response of vibrations induced in the bone through the technique shown in FIG. 1.

As shown in FIGS. 1 and 2, the inventor's first technique for measuring bone density includes the step of inducing a vibration in the bone which is desired to be measured, for example by striking the flesh of a patient's arm 20 with a blunt instrument such as a rod 22 to induce vibrations in a bone 24 within the patient's arm. For convenience, the opposite ends of the patient's arm 20 may be supported by a pair of supports 32, 34. A mechano-electrical vibration transducer 26 measures the induced vibration of the bone 24 and produces an electrical output which may be amplified by an amplifier 28 and then input to a computer 30 for calculation of the modal damping factor.

As shown in FIG. 2, the vibration induced by the input of an impulse of energy into the arm 20 will have a different initial amplitude corresponding to varying input force levels. However, the ratio of the amplitudes of the first and second cycles of vibration ($A_1/A_2$) is invariant with respect to the level of the force input to the bone. Thus, the modal damping factor may be calculated by comparing the amplitudes of successive cycles of vibration induced by any of these input force levels. As shown in FIG. 2, the intensity of the blow to the arm does not affect the measurement of the modal damping factor as the modal damping factor is determined by comparing two successive amplitudes and the ratio of two successive amplitudes is constant regardless of their size. Whether the initial amplitude has an intensity of a, b, or c, there is no variation in the measured modal damping factor. Instead, the modal damping factor of the bone 24 is predominantly dependent on the characteristics of the bone.

Figure 3:
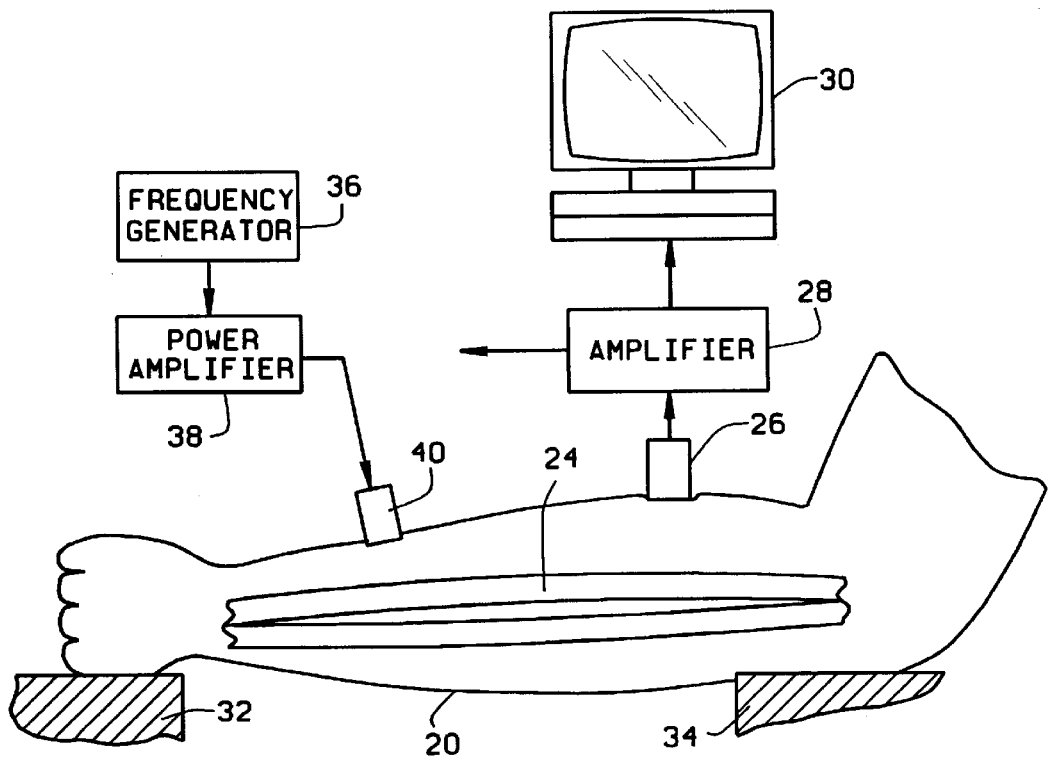
FIG. 3 is a diagrammatic view of a second technique for measuring bone density through the coupling of a continuous energy source to the bone.
Figure 4:
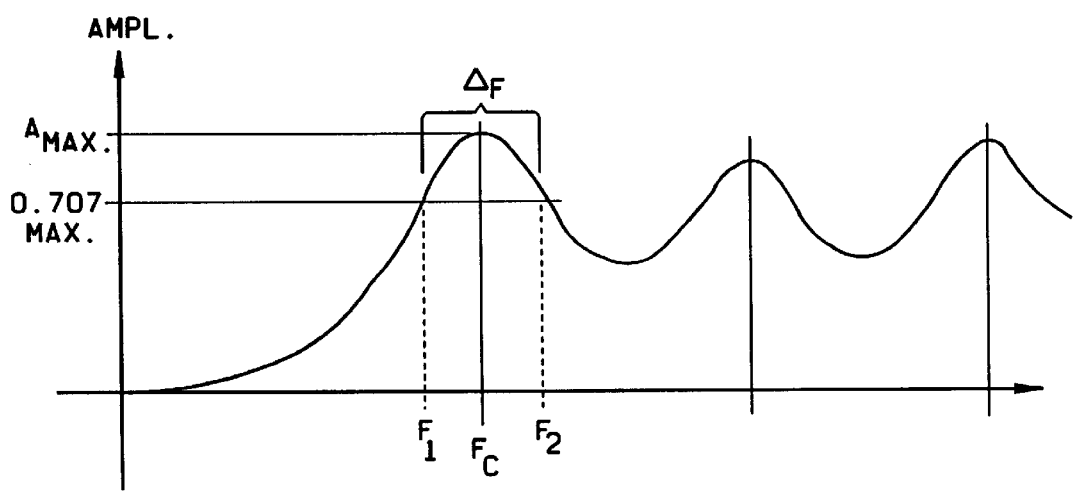
FIG. 4 is a graph of the vibrational response induced in the bone using the technique of FIG. 3.

As shown in FIGS. 3 and 4, an alternate technique for measuring bone modal damping factor may be used. As before, the patient's arm 20 has a bone 24 surrounded by the flesh to which a mechano-electrical vibration transducer 26 is mounted for converting the sensed vibrational response to an electrical signal which may be amplified by an amplifier 28 and input to a computer 30. However, the initial energy input to the patient's arm 20 is achieved by way of a frequency generator 36 which produces an electrical output at a particular frequency which is amplified by a power amplifier 38 which amplifies the output from the frequency generator to a particular amplitude. The output from the power amplifier 38 is fed to a second transducer 40, which may be a speaker or shaker or other such electro-mechanical vibration transducer coupled to the patient's arm 20. The frequency generator 36 is then tuned to frequencies sweeping through a range of the lower natural frequencies of the particular patient's particular bone 24 being measured to produce a continuous vibrational response as shown in FIG. 4. A maximum amplitude of one of the several natural frequencies induced in the patient's bone 24 is chosen for measurement of the modal damping factor. As is well known in the art, the modal damping factor is equal to the half power bandwidth, $\Delta F$, or $F2-F1$, divided by the center frequency $F_c$. The center frequency, $F_c$, is the frequency at which the maximum amplitude occurs. The half power frequencies, F1 and F2, are those frequencies at which the amplitude is $(\sqrt{2})/2$, or about 0.707 times the maximum amplitude.

The inventor has conducted two separate experiments which prove the efficacy of utilizing the modal damping factor for measuring bone density. In a first experiment, chicken femoral bones were treated with hydrochloric acid for varying lengths of time, their mass was measured, and then their modal damping factor was determined using techniques similar to those disclosed herein. Their modal damping factors were then compared with the modal damping factors of untreated chicken femoral bones. The modal damping factor directly correlated with the number of hours of acid treatment of the chicken femoral bones. This was to be expected as the longer the bones were immersed in the acid, the greater their porosity, the greater the reduction in their mass and hence the greater the reduction in their density. Furthermore, the change in modal damping factor was nearly one order of magnitude greater than the change in the measured density of the bone. Hence, the modal damping factor was considered to be highly sensitive to changes in density and thus a good parameter for measuring density as smaller changes in density could be readily detected.

In a second experiment, rat bones were used. More particularly, tibiae of two groups of rats were compared, one group having undergone an extensive training program. It being understood that training increases bone density which should cause a reduction in modal damping factor. Both groups included members which were relatively young, as well as members which were relatively old. In comparing the bones for the younger rats, it was found that training resulted in slightly lower bone density and higher damping ratio, but these changes were considered to be statistically insignificant. However, in the older rats, the average change in modal damping factor due to training was about forty percent while the change in density was about 23 percent. These experimental results suggest the beneficial results of physical exercise or training in older individuals of maintaining the mineral content and hence the density of the individual's bones. Again, the modal damping factor measurement was found to significantly correlate with bone density.

Figure 5:
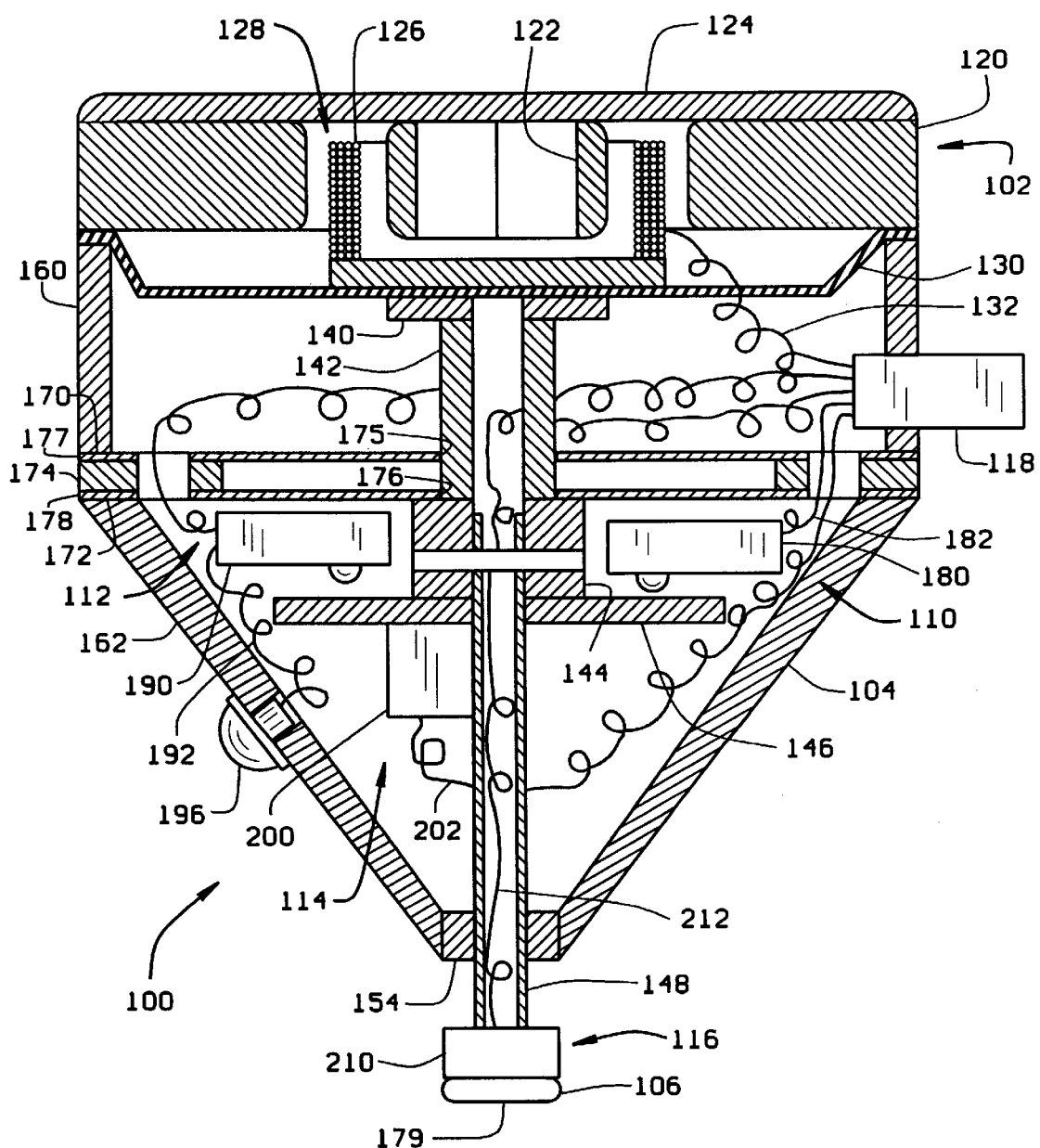
FIG. 5 is a cross-sectional view of a vibrator apparatus used as a continuous energy source to excite a bone in vivo.

Although various electro-mechanical vibration transducers 40 may be used in the second method described above and shown in FIG. 3, the inventor has succeeded in developing a vibrator apparatus 100 shown in FIG. 5 which is particularly well-suited to the task. The apparatus 100 is generally comprised of an electro-mechanical vibration transducer 102 mounted between a housing 104 and a pad 106 for vibrating the pad relative to the housing. Further, the apparatus 100 has several internal control and measurement circuits 110, 112, 114, 116 which determine when the transducer 102 vibrates, which signal the user, which measure the force with which the pad 106 is pressed against the patient and which measure the amplitude at which the pad vibrates relative to the housing 104, respectively. A connector 118 mounted on the housing 104 is used to communicate signals between the control and measurement circuits 110, 112, 114, 116 and various external systems such as frequency generators, amplifiers and computers.

The vibration transducer 102 of the preferred embodiment includes two concentric annular magnets 120, 122 joined by a flat magnetic plate 124 which in combination produce a complex magnetic field about the magnets. An electrical coil or coil driver 126 is positioned in the space 128 formed between the inner and outer annular magnets 122, 120 and is held in place by a resilient elastic diaphragm 130 positioned adjacent the magnets and opposite the magnetic plate 124. The electrical coil 126 is a single strand of wire wound about an axis as is well-known in electro-mechanical devices. Electrical leads 132 are connected to each end of the single strand of wire in the electrical coil 126 and extend through the housing 104 to the connector 118 so that the coil may be energized from a source external to the vibrator apparatus 100. Note that FIG. 5 represents each electrical lead with a single thickness curling line. Nonetheless, all of the leads in the apparatus 100, including leads 132, are two-wire insulated parallel conductors in the best mode.

Due to what is known as the Faraday effect, when an electrical current passes through the coil 126, a magnetic field is induced about the coil. Depending upon the polarity of the electrical current, the magnetic field induced about the coil 126 will either attract or repel the coil toward or away from the complex magnetic field surrounding the permanent magnets 120, 122, 124. If an alternating current passes through the coil 126, the coil will alternately be attracted and repelled by the magnetic field of the magnets 120, 122, 124. Because the coil 126 is mounted on the resilient diaphragm 130, the coil displaces toward and away from the magnets 120, 122, 124 as the alternating current passes through the coil. Thus, the coil 126 oscillates back and forth in the space 128 between the inner and outer magnets 122, 120 as the polarity of the alternating current changes over time. The frequency and amplitude of the coil 126 oscillation varies with changes in the frequency and amplitude of the alternating current. Depending upon the system dynamic characteristics, the frequency of the coil 126 oscillation may be equal to the frequency of the alternating current, but need not be. Likewise, the coil 126 displacement amplitude may linearly vary with respect to the amplitude of the alternating current, but need not. Although the particular structure described above is used in the preferred embodiment, other embodiments as are well known in the art are also within the scope of this invention. For instance, the magnets 120, 122, 124 may be replaced with a ferrous material provided that the mean of the alternating current is shifted to produce a constant polarity alternating current. Further, the entire structure may be replaced with a common "off-the-shelf" acoustical speaker.

As shown in FIG. 5, an annular disk 140 is attached to the diaphragm 130 opposite the coil 126 and a hollow cylinder 142 extends from the disk toward the center of the housing 104 where the cylinder connects to a collar 144 and a circular ring 146. A hollow rod 148 is connected to the collar 144 with a pin 150 and extends through the housing 104 opposite the magnetic plate 124. Each of these connections may be made in any of a variety of ways as are well known in the art, such as by screw fastening, brazing, welding, adhesively bonding, etc. Likewise, although a pin 150 is used in the preferred embodiment to connect the rod 148 to the collar 144, other fastening means may be used and are within the scope of this invention. The pad 106 is positioned at the distal end of the rod 148 and has a circular configuration with rounded corners. Because the magnets 120, 122, 124 are connected to the housing 104 and the pad 106 is connected to the coil 126, the pad oscillates relative to the housing when the coil oscillates relative to the magnets. A bushing 154 seals the space between the housing 104 and the rod 148 to prevent contaminants from entering the housing. The bushing 154 also prevents lateral movement and wear between the rod 148 and the housing 104 to improve the life and performance of the apparatus 100.

The housing 104 is comprised of a cylindrical portion 160 which is sized to fit in the palm of the user's hand and a conical portion 162, the apex of which is adjacent the pad 106. The shape of the conical portion 162 gives a better line of sight to the pad 106 than would otherwise be available if a non-tapered shape where used. The line of sight permits visual confirmation of the location of the pad 106 as the cylindrical portion 160 is held in the user's hand. Although the housing 104 of the preferred embodiment is sized and shaped to be hand-held, the housing may alternatively be sized and shaped to be mounted in a robotic or stationary fixture without departing from the scope of this invention.

The electro-mechanical vibration transducer 102 and vibrator apparatus 100 described above is fairly typical of those found in the prior art. However, the control and measurement circuits 110, 112, 114, 116 of the vibrator apparatus described below depart from typical vibration devices and make this vibrator apparatus exceptionally well suited to the task of exciting a patient's bone in vivo.

Two annular plate springs 170, 172 spaced by an annular spacer 174 are attached to the cylinder 142 and to the housing 104. The cylinder 142 is attached to the inner diametral edges 175, 176 of the annular springs 170, 172 and the housing 104 is attached to the outer diametral edges 177, 178 of the springs. As shown in FIG. 5, the springs 170, 172 are positioned intermediate the ends of the cylinder 142 and near the intersection of the cylindrical and conical portions 160, 162 of the housing 104. Although any elastic material may be used for the springs 170, 172, a generally linearly elastic material is used in the preferred embodiment so that the spring properties and dynamic characteristics are easily evaluated. The springs 170, 172 bias the cylinder 142 toward an equilibrium position with respect to the housing 104 wherein both springs are substantially planar and undeflected. However, the pad 106 may be pushed toward the housing to deflect the springs 170, 172 away from their equilibrium positions. Because the springs have a generally linear spring constant, the displacement of the pad 106 relative to the housing 104 is proportional to the force with which the pad is pushed toward the housing. The pad 106 has a constant surface area 179 configured to be pressed against a patient's flesh. When the pad 106 is pressed, the normal pressure against the pad is equal to the force with which the pad is pushed multiplied by the surface area 179. Thus, because the displacement of the pad is proportional to the force and the pad surface area 179 is constant, the displacement is also proportional to the pressure with which the pad is pressed against the patient's flesh.

A switch 180 is positioned within the housing 104 and adjacent the ring 146 so that the ring actuates the switch when the ring travels a predetermined distance relative to the housing. Because the distance traveled is proportional to the pressure with which the pad 106 is pressed, the switch 180 may be set to actuate when a minimum predetermined pressure is achieved between the pad and the patient's flesh. Actuation of the switch 180 closes the circuit within the switch to permit electrical current to pass through the switch. Leads 182 extend from each side of the circuit within the switch 180 and may extend to the connector 118 mounted on the housing. By placing the switch 180 in series with the electro-mechanical vibration transducer 102, the apparatus 100 may be configured to only vibrate when a predetermined minimum pressure is achieved between the patient's flesh and the pad 106. Together the switch 180 and springs 170, 172 form the pressure-vibration control 110 which determines when the transducer 102 vibrates. As appreciated by those in the art, the control 110 is a mechano-electrical force transducer. The value of the minimum predetermined pressure may be changed or adjusted by moving the switch 180 relative to the housing. Thus, the switch 180 may be adjustably mounted to the housing in any of several ways which are well-known in the art.

The over-pressure control 112 works similarly to the pressure-vibration control 110 and is a second mechano-electrical force transducer. The control 112 includes a second switch 190 mounted within the housing 104 and adjacent the ring 146 so that the switch closes when a maximum predetermined pressure is applied to the pad 106. Leads 192 extending from the switch 190 connect the switch to a light emitting diode (LED) 196 or other display or signal device to alert the user that the maximum predetermined pressure has been reached and/or exceeded. In this way, the user may be alerted that the pressure between the pad 106 and the patient's flesh is higher than needed and may be so high as to cause contusions or lacerations or other undesirable side effects. Similarly to switch 180, switch 190 may be adjustably mounted to permit the maximum predetermined pressure to be adjusted.

The displacement sensor 114 includes a mechano-electrical vibration transducer 200 positioned between the housing 104 and the ring 146 to measure the displacement of the pad 106 relative to the housing. As is well known in the art, mechano-electrical vibration transducers sense displacement and output an electrical signal which is linearly proportional to the sensed displacement. Leads 202 extend from the mechano-electrical vibration transducer 200 to the connector 118 so that the amplitude of the vibratory oscillations of the pad 106 may be monitored external to the vibrator apparatus 100. Thus, the system dynamic characteristics of the apparatus 100 need not be known or even linear with respect to the alternating current input to determine the frequency and amplitude of the pad 106 oscillations relative to the housing 104.

The force sensor 116 includes a force transducer 210 positioned between the rod 148 and pad 106 so that the force transmitted through the rod may be measured. Leads 212 extend from the transducer 210 to the connector 118 to permit the sensed force data to be transmitted external to the housing 104. As previously described, the force in the rod 148 is proportional to the pressure with which the pad 106 is applied to the flesh of the patient.

To operate the vibrator apparatus 100 described above, a user such as a nurse or medical technician holds the cylindrical portion 160 of the housing 104 in the palm of their hand and presses the pad 106 against the patient's flesh. As mentioned previously, the conical shape of the conical portion 162 of the housing 104 permits the user to visually confirm where the pad 106 is being pressed with respect to the patient's flesh. As the pressure between the pad 106 and the patient's flesh increases, the ring 146 deflects toward the switches 180, 190 (upward as shown in FIG. 5) until the ring actuates switch 180 which is in series with the electromechanical vibration transducer 102 and the circuit within the switch closes to permit electrical current to pass through the coil 126. Because the electrical current is an alternating electrical current, the coil 146 and pad 106 oscillate as previously described when the pad is pressed against the patient's flesh with a pressure equal to or greater than the minimum predetermined pressure. When the user presses the pad 106 against the patient's flesh with an increased pressure, the pressure may exceed the predetermined pressure at which complications or discomfort may begin. When this maximum predetermined pressure is achieved, the other switch 190 is actuated to energize and illuminate the LED 196. This signals the user to reduce the pressure in order to avoid these unwanted complications.

The advantage of pressing the pad 106 against the patient's flesh is that the flesh is compressed which reduces the dynamic response of the flesh to the vibration input. When the flesh is compressed, the dynamic response of the flesh is damped and the natural frequency of the flesh is increased because the effective stiffness of the flesh is increased. In addition, the vibrator apparatus 100 oscillates the pad 106 at frequencies which are lower than the natural frequencies of the compressed flesh but which are within the range of the lower natural frequencies of the bone being measured. Thus, the flesh is not excited by the vibratory input from the vibration transducer 102 but the bone is excited. Further, the flesh response is damped so its amplitude is small relative to the amplitude of the bone response. In this way, the response of the bone is "decoupled" from the response of the flesh. Thus, the noise in the response which occurred when using prior art vibrator apparatus due to the flesh vibrating independently of the bone is virtually eliminated, leaving a relatively clean signal which may be easily analyzed to determine the modal damping factor of the bone alone.

The signals output through the connector 118 may be transmitted to an external control (not shown) and/or to a computer for detailed analysis of both the excitation and the response. Alternatively, the signals may be stored in a data collection device (not shown) for later and/or remote data reduction and analysis. In the preferred embodiment, the response to the excitation is analyzed using a microprocessor connected to the vibrator apparatus 100 external to the housing 104.

The microprocessor of the preferred embodiment uses the following algorithm to analyze the response to the continuous excitation:
The microprocessor may be based on a PENTIUM processor chip or the like as is well known in the art. PENTIUM is a U.S. registered trademark of the Intel Corporation.

The frequency of the input is varied over time and the response is sampled over a range of input frequencies. These responses are stored as values representing the amplitude of displacement taken at spaced time intervals corresponding with the sampling rate. These stored amplitude values lay on a curve like that shown in FIG. 4 and may be processed as described above with respect to the second method of determining modal damping factor. Because of minor noise in the response signal as well as the discrete rather than continuous sampling used, the center frequency and half power frequencies of the stored data are difficult to determine with the precision desired. Thus, the data is matched to an idealized theoretical response and the modal damping factor of the response is estimated as the modal damping factor of the theoretical system.

The system dynamics calculations are simplified by idealizing the behavior of the bone and flesh as a one degree of freedom system with simple second order response as is well understood in the art. This idealization is fairly accurate if an excitation source such as the vibrator apparatus 100 is used because the bone and flesh are decoupled and the bone dominates the response at the lower natural frequencies. For such an idealized system, the amplitude of the response, $Y_i$, varies with the input frequency, $\omega_i$, as follows:

$$y_i = \frac{2x_{max}\zeta\sqrt{1-\zeta^2}}{\sqrt{\left[\left(\frac{\omega_i}{\omega_n}\right)^2 - 1\right]^2 + \left(2\zeta\frac{\omega_i}{\omega_n}\right)^2}}$$

were $x_{max}$ equals the maximum theoretical amplitude which occurs at the center frequency, $F_c$, of the particular mode being analyzed. As described earlier, $\zeta$ is the modal damping factor of the bone for the mode being analyzed, and $\omega_n$ is the natural frequency in radians per second of the bone at the maximum theoretical amplitude, $x_{max}$. It is readily apparent that $\omega_n$ and $F_c$ are different expressions for the same quantity; however, one is expressed in cycles per second ($F_c$) and the other is expressed in radians per second ($\omega_n$).

The computer algorithm above minimizes the difference between the measured amplitudes and the theoretical amplitudes by varying the maximum amplitude ($x_{max}$), the modal damping factor ($\zeta$), and the natural frequency ($\omega_n$). As is common in the art, the difference or error between the samples and the theoretical amplitudes is evaluated by summing the squares of the differences of the values over the entire range of samples. Although many different iterative numerical analysis techniques could be used, the inventor uses the Newton-Raphson iteration method to minimize the error. The Newton-Raphson method, also known as Newton's method, is an iterative process whereby an initial value or guess for a solution is assumed and a next value or improved guess is calculated by adjusting the previous guess by an increment equal to the quantity of the function at the last guess divided by the slope of the function at the last guess. In other words, $$x_{n+1} = x_n - \frac{f(x_n)}{f'(x_n)}$$

This iteration method is used because of its simplicity and relative speed of convergence to a solution. As with any iterative analytical approach, the process of improving the guess is repeated until the guess converges to a solution having an error less than some specified value. Because of the nomenclature used in many common computer languages, each iterative process is commonly referred to as a "do-loop".

In the first do-loop of the algorithm above, the Newton-Raphson method is used to obtain a good initial guess for the modal damping factor. The natural frequency and maximum amplitude are held constant while the modal damping factor is varied until the amount of change in modal damping factor is within a specified value (i.e., "|correction|<preset value"). Once this improved initial guess is found, the algorithm continues to a second do-loop.

In the second do-loop, the Newton-Raphson method is again used; however, this time the modal damping factor, natural frequency and maximum amplitude are each varied and a separate value for the error and the change in error with respect to the change in each of the three parameters is calculated. The parameters are varied until the sum of the squares of the differences of the errors is minimized. When the sum is minimized, the theoretical amplitudes are close to the sample amplitudes over the entire range of samples. Thus, the theoretical modal damping factor and the theoretical natural frequency when the sum of the squares of the differences in the errors is minimized are a good estimate of the actual modal damping factor and natural frequency of the bone being analyzed. Therefore, a modal damping factor may be accurately estimated for the system even though the system response has small noise fluctuations and is only discretely sampled.

It should be readily appreciated that other iterative analysis and/or curve fitting techniques may also be used to minimize the difference between the measured and theoretical amplitudes and modal damping factors. Further, the Newton-Raphson method may be used in different ways to arrive at a solution. For instance, the first do-loop for finding an improved initial guess for modal damping factor could be eliminated if desired or supplanted by other do-loops in which improved initial guesses for natural frequency or maximum amplitude are found. Likewise, other error evaluation techniques can be used to measure the error between the theoretical and measured amplitudes. Yet another variation of the analysis technique is to use a simplified higher degree of freedom system or higher order system approximation for the theoretical amplitude calculation. Each of these variations in analysis technique are within the scope of this invention.

In addition, there are various other changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for estimating a modal damping factor of a bone positioned within the flesh in an organism, the method comprising the steps of:

dynamically isolating the bone from the flesh;

vibrating the isolated bone at a plurality of frequencies and through a plurality of cycles of displacement at each of the plurality of frequencies, each of the plurality of cycles of displacement having a substantially constant amplitude at each of the plurality of frequencies;

measuring the amplitude at which the bone vibrates at each of the plurality of frequencies; and calculating the modal damping factor from the measured amplitudes.

2. The method of claim 1 wherein:

the step of calculating the modal damping factor includes the steps of:

assuming a modal damping factor, a damped natural frequency and a maximum amplitude;

calculating a theoretical amplitude at each of the plurality of frequencies from the assumed modal damping factor, the assumed damping natural frequency and the assumed maximum amplitude;

comparing the theoretical amplitudes with the measured amplitudes;

adjusting the assumed modal damping factor, the assumed damped natural frequency and the assumed maximum amplitude; and repeating the steps of calculating, comparing and adjusting until the theoretical amplitudes and the measured amplitudes are within a predetermined level of agreement.

3. The method of claim 2 wherein:

the step of comparing the theoretical amplitudes with the measured amplitudes includes the steps of:

subtracting one of the theoretical and measured amplitudes from the other of the theoretical and measured amplitudes at each of the plurality of frequencies to obtain a difference at each of the plurality of frequencies;

squaring the differences at each of the plurality of frequencies to obtain a sum at each of the plurality of frequencies; and adding each of the sums together to obtain a summation over all of the frequencies.

4. The method of claim 2 wherein:

the step of adjusting the assumed modal damping factor, the assumed damped natural frequency and the assumed maximum amplitude includes the steps of:

calculating a first representative error by comparing the theoretical amplitude obtained from the first assumed modal damping factor with the measured amplitude;

incrementing the first assumed modal damping factor to obtain a second assumed modal damping factor;

calculating a second theoretical amplitude from the second assumed modal damping factor;

subtracting the first assumed modal damping factor from the second assumed modal damping factor to obtain a difference in assumed modal damping factor;

calculating a second representative error by comparing the second theoretical amplitude obtained from the second assumed modal damping factor with the measured amplitude;

subtracting the first representative error from the second representative error to obtain a difference in representative error;

multiplying the difference in assumed modal damping factor by the first representative error to obtain a quantity;

dividing the quantity by the difference in representative error to obtain a quotient; and calculating an adjusted assumed modal damping factor by subtracting the quotient from the assumed modal damping factor.

5. A device for determining an integrity of a discrete piece of hard tissue in a human, said device including a contact element adapted to contact a portion of a patient's body, a vibrator coupled to said contact element, a displacement sensor for measuring the displacement of said contact element, an indicator, and a pressure sensor for activating said indicator when the pressure between said device and said portion of the patient's body exceeds a predetermined limit.

6. The device of claim 5 further comprising a connector for coupling at least one of said vibrator and said displacement sensor to a microprocessor.

7. The device of claim 6 further comprising a microprocessor.

8. The device of claim 5 wherein said contact element includes a spring-mounted rod, said pressure sensor includes a limit switch actuated by said rod, and said vibrator is configured to induce reciprocating motion in said rod.

9. The device of claim 5 wherein said predetermined limit is adjustable.

10. The device of claim 5 further comprising a force sensor for measuring the force applied to said contact element.

* * * * *